United States Patent [19]
Carter

[11] Patent Number: 5,958,718
[45] Date of Patent: Sep. 28, 1999

[54] DIAGNOSIS AND TREATMENT OF NEURO-COGNITIVE DISORDERS ASSOCIATED WITH SYSTEMIC IMMUNOLOGICAL MALFUNCTION

[75] Inventor: William A. Carter, Birchrunville, Pa.

[73] Assignee: HEMISPHERx Biopharma, Inc., Philadelphia, Pa.

[21] Appl. No.: 08/905,957

[22] Filed: Aug. 5, 1997

Related U.S. Application Data

[63] Continuation of application No. 08/392,620, Feb. 22, 1995, abandoned, which is a continuation of application No. 08/161,700, Dec. 6, 1993, abandoned, which is a continuation of application No. 07/908,902, Jul. 2, 1992, abandoned, which is a continuation of application No. 07/504,185, Apr. 4, 1990, abandoned, which is a continuation-in-part of application No. 07/421,596, Oct. 16, 1989, abandoned.

[51] Int. Cl.$^6$ .............................. C12Q 1/34; C12N 9/22
[52] U.S. Cl. ................................... 435/19; 435/4; 435/18; 435/199
[58] Field of Search ..................... 435/4, 18, 19

[56] References Cited

FOREIGN PATENT DOCUMENTS

A-0 306 347  3/1989  European Pat. Off. .
A-0 308 066  3/1989  European Pat. Off. .
A-0 350 151  1/1990  European Pat. Off. .

OTHER PUBLICATIONS

Krust et al. *Virology.* 120. pp. 240–246. 1982.

Ohmann et al. *Journal of Interferon Research.* vol. 9. pp. 159–166. 1989.

Jiang et al. *Journal of Biological Chemistry.* vol. 263, No. 35. pp. 19154–19158.

*Primary Examiner*—Leon B. Lankford, Jr.
*Attorney, Agent, or Firm*—Nixon & Vanderhye

[57] ABSTRACT

The presence of neuro-cognitive disorders associated with systemic immunological malfunction are assessed in human patients by determining the level of intracellular RNase L in a sample of the patient's peripheral blood and comparing that level to predetermined levels of RNase L in healthy individuals. Aberrant RNase L levels as compared with those in healthy individuals indicate the presence of neuro-cognitive disorders associated with systemic immunological malfunction. This procedure is useful to distinguish systemic immunological malfunction from primary psychological or neuropsychiatric disorders presenting otherwise similar clinical symptoms.

2 Claims, No Drawings

DIAGNOSIS AND TREATMENT OF NEURO-COGNITIVE DISORDERS ASSOCIATED WITH SYSTEMIC IMMUNOLOGICAL MALFUNCTION

CROSS-REFERENCE TO RELATED APPLICATIONS

This is a continuation of application Ser. No. 08/392,620, filed Feb. 22, 1995, now abandoned which is a continuation of application Ser. No. 08/161,700, filed Dec. 6, 1993 which is a continuation of Ser. No. 07/908,902 filed Jul. 2, 1992 which is a continuation of Ser. No. 07/504,185 filed Apr. 4, 1990 which is a continuation-in-part of Ser. No. 07/421,596 filed Oct. 16, 1989, now abandoned.

This invention relates to procedures for diagnosing the presence of neuro-cognitive disorders for the type associated with systemic immunological malfunction and distinguishing same from primary psychological or neuropsychiatric disorders presenting similar clinical symptoms. The invention also includes diagnosing dementias of the type associated with immunological derangements. Therapeutic intervention for such conditions with dsRNAs is also described.

SUMMARY OF THE INVENTION

Central nervous system (CNS) manifestations of memory loss, reduction in intelligence quotient (IQ) and loss of cognitive skills may be associated with disturbances in 2'-5'A pathway metabolism in peripheral blood mononuclear cells (PBMC). These disturbances may signal underlying and clinically undetected release of lymphokines which, in turn, contribute to a clouded sensorium. Also, often at play as undetected retroviral infections and/or herpes infections. The occult viral infection also contributes to the brain pathology both directly and indirectly (by triggering inappropriate and chronic lymphokine production). The dual disease manifestations are diagnosed in a facile manner by examination of 2'-5'A pathway components and interventive therapy with dsRNAs which biologically neutralize the lymphokine toxicity while reducing the intrinsic viral burden.

I have found that certain dementias are the result of sustained immunological activation following an unresolved virus infection, which perpetuates the memory loss. I have also observed malaise and depression. Elevated serum levels of various lymphokines, such as IL-2, IL-6, TNF and interferon which are associated with bodily defenses, and these molecules (alone or collectively) appear to contribute to the symptomatology.

The ill-defined etiology of dementias (Alzheimer's disease, etc.), has contributed heretofore to a difficulty of discovering effective treatment for this disorder. Therefore, I developed a new strategy: first to define an abnormal cellular phenotype in dementia patients which may result in significantly impaired control over various immunological derangements including viral infections, without regard to the specific nature of the inciting organisms, and second, to determine if the abnormal phenotpe might be found in certain intracellular enzymatic pathways which confer an immunomodulatory antiviral state on human cells, including brain tissue. Such pathways are known and include the dsRNA dependent 2-5A synthetase/RNase L pathway and the dsRNA dependent protein kinase pathway. These enzymatic pathways are activated or deactivated by a variety of animal viruses, as well as by by-products of viral infection, such as interferon or dsRNA (double stranded RNA). The pathways, when properly regulated, elicit cellular resistance to a wide variety of pathogens because the resultant biochemical products can interfere with the synthesis and stability of pathogen components. I refer here to these enzymatic pathways as "ant iviral" pathways, but it should be noted that they have also been implicated in the differentiation of immune cells. In particular, these pathways may participate in the activation of T cells, B cells and monocytes or their precursor cells.

I previously noted abnormalities in the 2-5A synthetase/RNase L pathway in vivo in another chronic virus infection of human (ref. 1). For example, acquired immune deficiency syndrome (AIDS) caused by human immunodeficiency virus (HIV) is accompanied by abnormally high levels of latent 2-5A synthetase, reduced levels of bioactive 2-5A and low to undetectable levels of RNase L (ref. 1). This phenotype is consistent with a relatively inactive antiviral pathway owing to lack of appropriate activation of 2-5A and consequent absence of the product of 2-5A synthetase, 2-5A.

In my present study of dementia patients, herpes virus was also identified with monoclonal antibodies in some patients discussed below, while the remainder were monitored with sera containing antibodies against several herpeviruses. I will therefore refer to certain of the dementia patients as "virus positive by culture", rather than as HHV-6 positive. Novel retroviruses were also isolated from these and other patients with similar pathology of the CNS.

DETAILED DISCLOSURE OF THE INVENTION

I have discovered and hereby disclose that a hyperactive or an aberrance in the 2-5 A synthetase/RNase L pathway exists in individuals having any chronic dementia associated with metabolic disturbances, defects in neuro-cognition or chronic cerebral dysfunction (CCD). This derangement is often accompanied by other biochemical and gross tissue anomalies such as cerebral lesions revealed by imaging as well as cognitive deficits such as loss of IQ and impaired attention and abstraction ability. Further, the natural killer cell function and NK cell phenotype are often unusual in CCD patients.

These disorders are effectively treated with dsRNA therapy which normalizes and favorably adjusts the 2-5 A synthetase/RNase L pathway and restores a dsRNA deficit in the patient. Improvement is seen on both the cellular and functional levels with memory and IQ values restored to near or at previous levels while exercise tolerance and oxygen consumption are increased. Patients having chronic cerebral dysfunction were assessed using various techniques and procedures as explained below.

Severe Chronic Dementia Study

Fifteen patients having severe chronic dementia were given 200–400 mg Ampligen®, a mismatched double-stranded RNA with minimal side effects, twice a week for up to 24 weeks. Blood levels of 30–50 $\mu$g/ml Ampligen® were attained. Levels of 10 $\mu$g/ml were maintained for one hour or more in most patients. All 15 patients presented with abnormal antiviral 2-5A synthetase/RNase L pathway components in peripheral blood mononuclear cells. The components of this pathway returned toward more normal values during Ampligen® treatment. For example, bioactive 2'-5' oligoadenylage concentrations were 3–665 times normal (average=242) before treatment and declined in 13 patients to normal by 12 weeks. In 13 of 14 patients tested, evidence for reduction of culturable virus during therapy was also obtained and in 11 patients HHV-6 (human herpesvirus 6) and/or novel retroviruses was detected with monoclonal antibodies. The 15 patients displayed a highly-significant increase in performance status, as judged by improved Karnofsky scores, and most showed sustained improvements with regard to memory, IQ and other psychometric tests. No clinical significant toxicities were seen. Though mild flu-like symptoms can be observed, mismatched dsRNA therapy was well tolerated with no patient requiring dosage reduction.

In the majority of dementia patients, the abnormalitiy took the form of reduced levels of latent 2-5A synthetase and elevated levels of bioactive 2-5A and activated RNase L. This phenotype, which was markedly different from that following HIV infection, suggested hyperactivity of the antiviral pathway resulting from chronic overstimulation of the 2-5A synthetase. I describe herein clinical and virological improvements in dementia patients having certain of these 2-5A synthetase/RNase L antiviral pathway abnormalities during treatment with Ampligen®, a prototype dsRNA.

Patients—Patients had pretherapy Karnofsky performance scores of 60 or below. Patients exhibited persistent (or relapsing) debilitating dementia severe enough to reduce or impair average daily activity below 50% of their premorbid activity level for a period of at least 24 months, with no other clinical conditions that might have produced similar symptoms. An extensive medical workup excluded other possible causes including brain tumors, vascular abnormalities, situational depressions or other primary psychiatric disorders, as well as infectious diseases of non-viral origin. All patients gave evidence of dementia by lower than normal scores on the Wechsler Memory Scale and lower than expected full scale IQ scores (Wechsler Adult Intelligence Scale—Revised, WAIS-R), base on the patient's academic background and/or past performance on similar tests. In addition, these individuals exhibited greater than a two standard deviation range in scores of individual tasks within the WAIS-R test. Typically patients displayed an abnormal magnetic resonance imaging (MRI) scan of the brain on 1.4 Tesla MRI scanning.

Drug Regimens—Patients initially received 200 mg doses of Ampligen® (HEM Research, Rockville, Md., USA); administered intravenously twice a week for various periods of time (see Table 1), after which the dose was escalated to 400 mg twice weekly.

2-5A Pathway Mesurements and Virus Culture—These measurements were performed on blinded samples in central laboratories. The 2-5A synthetase/RNase L antiviral pathway was studied as follows. 2-5A synthetase was purified from PBMC extracts by poly(I).poly(C) agarose affinity chromatography (ref. 2). Only latent 2-5A synthetase was purified by this procedure, since enzyme occupied by dsRNA did not bind. The percent conversion of ATP to 2-5A, measured by thin layer chromatography, was then used to quantitate the activity of affinity-purified, latent 2-5A synthetase. Activated RNase L in PBMC extracts was determined by its ability to cleave ribosomal RNA (rRNA) to specific cleavage products, measured by electrophoresis (ref. 3). These assays were quantitated by densitometer scanning and were expressed as % of 18S rRNA cleaved/dilution of the extract. 2-5A was recovered from PBMC extracts by extraction with ethanol. Bioactive 2-5A was then estimated by its ability to activate purified latent RNase L to degrade poly(U)[$^{32}p_pC_p$] to acid soluble products.

Virus culture is described generally (ref. 4) for herpes viruses. Measurements involved preparing peripheral blood mononuclear cells from patients and culturing them for up to 30 days, periodically examining cultures for the presence of giant cells characteristic of herpesvirus infection. The presence of virus in giant cells was confirmed in some patients by immunofluorescence, using sera from patients with relatively high titers of antibodies against human herpevirus-6 (HHV-6). HHV-6 specific monoclonal antibodies were also used. The number of giant cells obtained after culture was related to virus load in vivo. To quantify virus load, cultures showing >10% of cells to be giant cells were scored $2^+$, those showing between 0% and 10% were scored $1^+$, and those showing no giant cells were scored 0. Decreases in virus load were also evaluated by monitoring the frequency of negative cultures after Ampligen® treatment.

dsRNA Blood Levels—Ampligen® blood levels were determined as described (ref. 5). Heparinized blood (100 $\mu$l) was mixed with 162 $\mu$l of 6 M GuSCN/0.1 M EDTA, pH 8 and incubated with a $^3$H labelled poly(C) probe. After hybridization, the uiipaired probe was eliminated with RNase and hybridized probe was precipitated and collected by filtration. The amount of hybridized probe was converted to an equivalent amount of Ampligen® by reference to a standard curve consisting of known amounts of Ampligen® added to heparinized blood and processed as described above. To measure elimination of Ampligen® from blood, blood was drawn at various times after the end of the infusion from the arm opposite that used for infusion.

Neuropsychological Testng—Each patient completed a battery of cognitive/neuropsychological function tests, including the Wais-R full scale IQ test, as well as the Halstead-Reitan Neuropsychological tests, and the Immediate Verbal, Delayed Verbal, Immediate Visual and Delayed Visual components of the Wechsler Memory Scale. Wechsler Memory scores reported here are Verbal score x2 plus visual scores. To avoid a potential "training effect", alternative forms of the Wechsler Memory Scalse were introduced over time.

Treadmill Exercise Test—Certain patients, though not all, with dementia, experience profound inability to perform routine exercise. Therapeutic improvements in CNS function were often associated with more normal activities of daily living including increased exercise. Treadmill exercise tolerance testing was conducted according to the Modified Bruce Protocol, with aerobic fitness being estimated according to standard equations by expired gas exchange with $O_2$ and $CO_2$ electrodes. $O_2$ consumption was measured at the anaerobic threshold, in order to eliminate motivation as a faetor.

The first dementia patient to receive Ampligen® was chronically ill with progressive debilitation and thus was felt to have a limited life expectancy. Specifically, though she was formerly a professional golfer, she had been unable to care for herself for approximately five hears, was unable to walk 25 feet without assistance, and had experienced increasingly frequent seizures. She was unable to read or even follow television due to lack of short term memory. She demonstrated NK dysfunction, virus culture positivity, an abnormal MRI scan, markedly impaired psychometric testing and low exercise tolerance (Table 1). She exhibited reduction of circulating virus within 8 weeks of starting therapy. Her Karnofsky score improved from 30 pretherapy to 80 after receiving Ampligen® for 24 weeks. Clinical improvements were seen in the areas of psychometric testing and exercise tolerance (Table 1). She exhibited reduction of circulating virus within eight weeks of starting therapy. Her Karnofsky score improved from 30 pretherapy to 80 after receiving Ampligen® for 24 weeks. Clinical improvements were seen in the areas of psychometric testing and exercise tolerance (Table 1 and Table 3). The patient how has a sustained improvement and is leading a normal life, fully self-sufficient, having been on Ampligen® for 18 consecutive months.

Immunomodulatory Virological Changes—Including patient 00, all 15 patients presented with a perturbed antiviral pathway within their peripheral blood mononuclear cells. Specifically, all 15 patients had altered levels of bioactive 2-5A in blood mononuclear cells. This was corroborated by altered RNase L activity in 13 patients. Twelve patients also had altered levels of latent 2-5A synthetase in peripheral blood cells at the onset of therapy. In all, 11 cases had a pretherapy antiviral pathway phenotype characterized by: (a) low levels of latent 2-5A synthetase, accompanied by (b) elevated amounts of bioactive 2-5A, and (c) abnormally high activity of RNase L. I term this the "profile 1 phenotype", a phenotype which is consistent with chronic stimulation of the pathway due to extracellular lymphokines. Two patients, patients 01 and 06, presented with elevated levels of latent 2-5A synthetase accompanied by elevated amounts of bioactive 2-5A and normal or elevated RNase L levels ("profile 2 phenotype"). Elevated levels specific of later 2-5A synthetase have been reported with infection by Epstein-Barr Virus (EBV), and could indicate a coactive infection in patients 01 and 06. EVB reactivation in patients 01 and 06 was supported by serological evidence.

During Ampligen® treatment, the 2-5A pathway returned toward a normal phenotype. In 13 patients, bioactive 2-5A levels had fallen to normal by 12 weeks and had declined in the remaining two, while RNase L activities had been significantly reduced to only 1–2 times normal (Table 2). In most patients, latent 2-5A synthetase levels rose toward normal by 12 weeks (Table 2), but declined again over time. Many patients were positive for virus culture at baseline. Virus titers were reduced during Ampligen® treatment in most patients. In addition, patients 02, 03, 04, 06 and 10 became negative on three successive cultures after 28–40 weeks of Ampligen®. The antiviral pathway profile associated with low levels of latent 2-5A synthetase (profile 1) was accompanied by more rapid reduction in virus load during therapy; however virus load decreased in 10 of the 11 patients tested during 24 weeks of therapy regardless of the phenotype at study entry (Table 1). The ability of dsRNA to reduce simultaneously the level of different virus agents (retroviruses and DNA viruses) present in the subjects contributes to the magnitude of response.

Performance Status and Exercise Tolerance—Patients entering the study were significantly incapacitated, with an average Karnofsky score of 47. The average score improved to 67 after 12 weeks of therapy and to 79 in the 11 patients evaluated at 24 weeks (Table 3).

Certain patients participated in treadmill testing before and during Ampligen® therapy. The length of time the treadmill exercise could be performed and the maximum $O_2$ consumption during exercise testing were determined. By 24 weeks in the group as a whole, treadmill duration increased by 20% and maximum $O_2$ consumption during exercise doubled. Twelve of fifteen patients increased $O_2$ consumption by more than 50% (Table 3). One patient (01) improved by only 10% by 24 weeks and one patient (09), for whom only eight week data were available, declined 15%. Since $O_2$ consumption measurements were taken generously at the anaerobic threshold, improvements cannot be attributed primarily to increased motivation, as by "lifting" a situational depression.

Neurophysiological Testing—Twelve of the 15 patients entered the study with impaired short term memory, as evidenced by the Wechsler Memory Scale. Wechsler scores improved 63% in these patients during the study. The largest gains occurred in the verbal tasks as opposed to visual tasks, probably because the group started with lower verbal scores. All patients having reached 24 weeks improved to within normal limits in the visual portion of the Wechsler Scale. The improvements in the delayed tasks of the Wechsler Memory Scale suggest an improvement in interference memory, a deficit increasingly noticed in early dementias.

Gains in IQ were also noted. Full scale IQ increased by 12%, from 106 to 119. Performance IQ increased 19% while verbal IQ increased 10%. Considering patients treated for 24 weeks, increases in full scale IQ appeared to be more pronounced during the third 8 weeks (8%) than during the first or second (2 and 0%, respectively), suggesting that IQ gains may occur more slowly than improvements in immunology, performance, or short term memory.

Ampligen® Blood Levels and Adverse Events— Ampligen® blood levels were determined by molecular hybridization. Immediately following infusion of 400 mg, blood levels averaged 43 $\mu$g/ml, ranging from 31–75 $\mu$g/ml (Table 2). Blood levels approximately half as high were obtained by infusion of a 200 mg dose. In these and other patients the apparent elimination rate varied; however, blood levels of 20 $\mu$g/ml were typically maintained for at least 1 hour in the majority of patients.

No clinically significant side effects were seen in any of the patients during the study. One patient developed iron deficiency anemia secondary to multiple phlebotomies and required the institution of iron supplementations. The majority of patients reported increase in flu-like symptoms, including myalgias and headaches. There was not evidence of alternation of coagulation, blood chemistry, white blood cell count, liver and renal function, or other abnormalities throughout the course of this study.

Patients displayed signs of clinical improvement, performances and improved cerebral function. The earliest improvements were related to normalization of the 2-5A synthetase antiviral pathway and NKH1$^+$ cell numbers as well as reductions in apparent virus load in peripheral blood cells. In one patient (05) who received Ampligen® for only 8 weeks, virus titers did not fall during the immediate study period. This patient also exhibited delayed correction of the antiviral pathway abnormality. Patient 01 exhibited improvement in Karnofsky score during the first 24 weeks, deteriorating in other categories. This patient did not have the same 2-5A synthetase abnormality which characterized 13 of the 14 other patients. Patient 01 improved after 24 weeks. At 32 weeks, his IQ was 138 and his $CO_2$ uptake during treadmill testing was 1.56 l/min. Two patients who voluntarily discontinued Ampligen® have now deteriorated as noted by falling Karnofsky scores and decrease in exercise tolerance and neurocognition.

The patients studied here presented with significantly altered levels of bioactive 2-5A and changes in latent 2-5A synthetase and activated RNase L which suggest altered metabolism of their intraccellular enzyme pathways. I have observed such a "hyperactive" phenotype to be caused by by-products of virus infection, namely by chronic overproduction of inciting cytokines. Since only a small proportion of blood mononuclear cells are likely to be directly virus infected in these patients, hyperactivation of the pathway by viral infection itself is not likely. In any event, altered metabolism of the 2-5A synthetase/RNase L pathways is a useful marker for identifying patients with chronic dementias unrelated to primary psychiatric or cerebrovascular disturbances.

After Ampligen® therapy, bioactive 2-5A levels returned to normal as did levels of activated RNAse L. This result is secondary restoration of more normal cytokine production or changes in cytokine utilization of blood cells. Also the activity of the 2-5A synthetase/RNase L pathway is down regulated by other dsRNA activated protein kinase pathway.

Improvements in clinical symptoms accompanied virological improvement. Improvement in Karnofsky scores, Wechsler memory test, performance and IQ scores were noted at the earliest times analyzed and improvements continued for the duration of the study. The more dramatic gains in Karnofsky scores appear to have been made after doses were elevated to 400 mg of Ampligen®. The average Karnofsky score at entrance, 47, described patients incapable of working and requiring considerable assistance in carrying out daily activities at home. The Karnofsky score at 80 the plateau during the study period, described patients able to carry out normal activities at work and home with effort, but without assistance. Wechsler memory test showed the greatest gains relatively early (16 weeks), whereas IQ test scores tended to improve later.

In several areas, improvements observed during Ampligen® therapy were statistically significant during the 24 weeks. Reduction in bioactive 2-5A and activated RNase L were significant at the p<0.0001 level. Improvements in parameters associated with reduction of dementia associated fatigue were highly significant. Improved performance on the treadmill was significant at the p<0.01 level at 16 weeks and p<0.001 level at 24 weeks. Improvements in Karnofsky scores were significant at the p<0.001 level at 16 weeks and p<0.0001 at 24 weeks. Improvements in the Wechsler memory testing were significant at 16 and 24 weeks (p<0.02). Full scale IQ increases were also significant.

Most patients displayed the same dramatic improvement in lifestyle as was seen with the first case. Many were unable to care for themselves and, in fact, were unable to remember or to ambulate without assistance prior to therapy. By 24 weeks, many that stayed on therapy were leading a more normal lifestyle. Improvements occurred while patients were receiving Ampligen®. Furthermore, two patients who have discontinued Ampligen® for at least two months have deteriorated neurocognitively.

TABLE 1

PATIENT 00

| Test | Pre | Post[c] |
|---|---|---|
| Treadmill | | |
| duration | 1.5 min | 9 min |
| O$_2$ consumption | 1.15 units | 2.36 units |
| Karnofsky[a] | 30 | 80 |
| Wechsler memory[b] | 0.5 | 2.75 |
| Full Scale IQ | 88 | 134 |
| Halstead Reitan[b] | | |
| hand tapping | 0 | 3 |
| Trails A | 0 | 3 |
| Trails B | 0 | 3 |
| Wais-R | | |
| information | 11 | 16 |
| digit span | 8 | 16 |
| vocabulary | 12 | 16 |
| arithmetic | 5 | 14 |
| similarities | 9 | 12 |
| block design | 5 | 10 |
| digit symbol | 3 | 9 |

[a]reconstructed from clinical charts
[b]0 = severe, 1 = moderate impairment, 2 mild impairment, 3 = within normal limits
[c]10 months of therapy

TABLE 2

VIROLOGY AND AMPLIGEN BLOOD LEVELS

| | | | Antiviral Pathway | | | | | | |
|---|---|---|---|---|---|---|---|---|---|
| | wks at | Blood Ampligen | 2-5A synth. | | RNase L | | Virus culture | | |
| Pt | 200 mg | µg/ml | pre | post | pre | post | pre | post | pre | post |
| 00 | 8 | — | 0.15 | 1.20 | 165 | 33 | 6 | 1 | — | — |
| 01 | 15 | 38 | 3.51 | 2.40 | 665 | 6 | 1 | 2 | 2 | 1 |
| 02 | 14 | 52 | 0.45 | 0.30 | 67 | 1 | 19 | 1 | 2 | 0[c] |
| 03 | 15 | 47 | 0.30 | 0.60 | 665 | 1 | 40 | 1 | 2 | 0.5[c] |
| 04 | 24 | — | 0.20 | 0.40 | 50 | 1 | 1 | 2 | 2 | 0.5[c] |
| 05 | 10 | 36 | 0.25 | 1.1 | 200 | 1 | 13 | 1 | 1 | 2 |
| 06 | 10 | 42 | 1.57 | 0.9 | 85 | 1 | 20 | 2 | 2 | 0.5[c] |
| 07 | 9 | 31 | 0.25 | 0.5 | 335 | 1 | 20 | 1 | 2 | 0.5 |
| 08 | 9 | 45 | 0.35 | 0.9 | 16 | 1 | 19 | 1 | 2 | 1.5 |
| 09 | 9 | 48 | 0.10 | 1.1 | 665 | 1 | 30 | 1 | 2 | 1.5[c] |
| 10 | 9 | 52 | 0.25 | 0.6 | 165 | 1 | 30 | 0.5 | 2 | 0.5 |
| 11 | 2 | 35 | 0.50 | 0.56 | 335 | 1 | 30 | 0.2 | 1.5 | 0.5 |
| 12 | 2 | 75 | 0.40 | 1.37 | 3 | 1 | 30 | 0.3 | 1 | 0.5 |
| 13 | 2 | — | 0.45 | 0.83 | 50 | 1 | 10 | 1 | 2 | 1 |
| 14 | 2 | — | 0.10 | 0.28 | 167 | 1 | 30 | 2 | 2 | 1.5 |

[a]= Fraction of normal average. Post = 12 wks. Similar results were obtained at 24 wks.
[b]= Calculated as described in methods, virus culture values were on average of 2 successive cultures, on two successive days before starting treatment (pre) or at 20 and 24 weeks during treatment (post). Patients 11–14 "post" values represent the last two determinations, taken between 8 and 16 weeks.
[c]= Became negative on 3 successive occasions after 24 weeks.

TABLE 3

CLINICAL PARAMETERS

| Patient | Karnofsky | | | Treadmill VO$_2$ (l/min) | | Wechsler Memory Scores | | IQ | |
|---|---|---|---|---|---|---|---|---|---|
| | pre | 12 wk | 24 wk | pre | post | pre | post | pre | post |
| 00 | 30 | 60 | 80 | 1.15 | 2.36 | 11 | 63$^c$ | 88 | 134 |
| 01 | 60 | 60 | 80 | 1.07 | 1.15 | 91 | 64 | 146 | 124 |
| 02 | 40 | 50 | 80 | 0.21 | 1.31 | 64 | 64$^b$ | 122 | 124$^a$ |
| 03 | 40 | 70 | 80 | 0.21 | 1.13 | 29 | 73 | 117 | 150 |
| 04 | 50 | 70 | 80 | 1.85 | 3.56 | 58 | 73 | 103 | 121 |
| 05 | 50 | 60 | 70 | 0.32 | 0.57$^a$ | 14 | 50$^b$ | 98 | 101$^b$ |
| 06 | 60 | 70 | 80 | 0.60 | 2.35 | 18 | 40 | 106 | 116 |
| 07 | 50 | 60 | 80 | 1.86 | 3.08 | 68 | 87 | 117 | 131 |
| 08 | 60 | 70 | 80 | 0.87 | 2.17 | 34 | 53$^a$ | 94 | 102$^a$ |
| 09 | 40 | 50 | 70 | 0.90 | 0.78$^c$ | 40 | 46$^b$ | 95 | 102$^b$ |
| 10 | 50 | — | 80 | 0.60 | 1.52 | 64 | 79b | 119 | 127 |
| 11 | 50 | 80 | 80 | 0.33 | 1.27 | — | — | 84 | 96$^a$ |
| 12 | 40 | 80 | 80 | 0.21 | 1.34$^b$ | 39 | 57$^b$ | 96 | 109$^b$ |
| 13 | 60 | 80 | 80 | 1.28 | 1.67$^b$ | 77 | 89$^b$ | 116 | 139$^b$ |
| 14 | 20 | 80 | 80 | 0.06 | 1.31$^b$ | 24 | 69$^b$ | 89 | 108$^b$ |
| average | 47 | 67 | 79 | 0.76 | 1.70 | 38$^f$ | 62$^f$ | 106 | 119 |

$^a$= up to 8 wks only;
$^b$= up to 16 wks only;
$^c$= 32 wks or 60 wks (no 24 wk point).
$^f$= patients with abnormal Wechsler Memory Score at entrance (excluding patients 1,11,13).

Chronic Cerebral Dysfunction Study

I also studied group of patients suffering from an organic brain syndrome characterized by cerebral dysfunction were studied, some for more than 15 months. Following an infectious-like episode, they developed a novel post-infectious immune dysfunction characterized by progressive mental deterioration, associated with memory lapses, occasional seizures and loss of higher mental abilities (the so-called cognitive functions). Magnetic Resonance Imaging (MRI) of the brain, performed on patients complaining of cognitive problems, showed a variety of abnormalities of high signal intensities, including large patchy areas consistent with edema or demyelination. Peripheral blood cells showed enzymatic deficiencies in a novel antiviral pathway termed the double-stranded (ds) RNA linked 2-5 A/RNase L pathway. Treatment with an exogenous source of dsRNA caused improvement in cognitive function, performance, MRI and loss of the 2-5 A pathway deficit.

Chronic cerebral dysfunction (CCD) may occur in virtually any age group and is often associated with a post infectious disease episode thought to be viral in nature. Chronic cerebral dysfunction can occur following mononucleosis (ref. 6), brucellosis (ref. 7) or herpes-type 6 infections as well as other factors.

Loss of Cognitive Functions—As with the study reported above, a variety of neuropsychologic instruments are available and I have used them to study and define a subset of patients with chronic cerebral dysfunctions. A typical test battery used has included the Wechsler Adult Intelligence Scale Revised (WAIS-R), the Wechsler Memory Scale, Immediate and Delayed (WMS), the Minnesota Multiphasic Personality Inventory (MMPI) and similar tests. Patients with CCD typically have test scores which are 2 standard deviations or more below the mean; some patients have an average of all scores which are one standard deviations or more below the mean and an occasional patient has multiple scores which are at least 4 standard deviations below the mean. Often I also observed "abstraction ability" and their performance on "set switching tasks" to also be impaired. Memory impairment seems to be secondary to a difficulty with attention and abstraction. Several patients were unable to perform such simple tasks as to balance their check books or place a key to the front door into the lock in the right configuration. These measurable and consistent cognitive deficits are unlikely to be caused by malingering or purely psychologic reasons since they often are associated with a downhill course in which the patient eventually becomes bed-ridden and almost moribund. I have also discovered a novel biochemical defect associated with this disease.

Magnetic Resonance Imaging of the Brain—Most of the patients from whom MRI scans were obtained complained of cognitive problems. The MRI scans for this study were generally performed using a 1.5 T superconducting Signa Magnetic Resonance Imager manufactured by the General Electric Company.

77% of the patients examined had abnormal MR scans: primarily punctuate areas of high signal intensity, and sometimes larger patchy areas of high signal intensity, consistent with focal edema and/or demyelination. The subcortical white matter was affected most often, but lesions were seen in the deep white matter also.

There was a correlation between the anatomic area and the clinical presentation: for example, one patient with ataxia had lesions involving the cerebellum, nine patients with visual symptoms had lesions involving the occipital cortex, one patient with paresis had a lesion involving the contralateral internal capsule. In the several instances where MRI scans were repeated, lesions persisted until I intervened with dsRNA therapy.

NK (Natural Killer) Cell Phenotype and Function: An Immunological Derangement—The NK cell phenotype and function are often unusual Phenotype: The usually predominant NKH1+T3 subpopulation (a subtyping of lymphocytes determined with monoclonal antibodies) can be diminished, but was normal in control subjects including patients with situational depressions of a transient nature which are often improved by mood elevating drugs, change in environment, exercise, etc. Also, NK cell function (cytolytic activity against various target cell lines) was generously reduced in patients but usually not in the control subjects. This defective cycolytic activity was particularly prominent after stimulation with interleukin-2, and when the target cell line was an (Epstein-Barr virus) EBV-infected cell line (LAZ 388). I have now performed the first serial studies on such patients and observed that the phenotypic and functional abnormalities in NK cells changed as the patients' clinical course improved following treatment with a source of exogenous dsRNA.

Antiviral Defenses and Virologic Studies—I have also observed that the majority of these patients are infected with herpes-6, a relatively new class of herpes virus only recently described (ref. 4, discussed above), and never before associated with loss of mental capabilities. Earlier studies found the virus in cancer patients. The virus has been variously called HBLV (human B cell lymphocyte virus) or HHV-6 (human herpes virus-6). The main features of this virus are its icosahedral symmetry with about 162 capsomers and a lipid membrane. Infected cells develop into large refractive cells and some patients may have up to 20–30% or more of their circulating lymphocyte cells (a certain type of lymphocyte of bone marrow or thymus lineage) infected. Following dsRNA therapy for several months, the percentage of infected cells falls dramatically and is associated with clinical improvement in cognitive abilities. I have also found EB (Epstein-Barr) virus in many of these patients as well as a novel retrovirus similar (though different genetically) to HIV, a retrovirus causing acquired immune deficiency or AIDs.

Specimens from several patients I have studied indicate the intriguing possibility of "pseudotyping" as a means of spreading this disease. By pseudotyping, I refer, for example, to the coat of a herpes type 6 virus surrounding the genetic material for a retrovirus. This would give rise to a novel form of contagion where the infectious agent spreads epidemiologically through the population like a herpes virus but the genetic information being spread is actually that of a retrovirus. I have utilized a variety of genomic probes (ref. 8), coupled with serological and morphological considerations (ref. 9), to put forward this novel mechanism of biological spread leading ultimately to mental deterioration and morbidity.

I have also studied the 2-5 A/RNase L pathway in peripheral blood lymphocytes of 10 patients having CCD with both MRI lesions and neurological deficits associated with a decreased intelligence quotient. In the first phase of the study, I looked at the antiviral defenses of patients with only intelligence quotients (IQs) equal or less than 105 whose prior occupation strongly suggested a higher premorbid IQ; in many patients I was able to locate tangible evidence revealing a higher IQ either months or years before the present cerebral illness.

Eight out of ten patients had a hyperactive or aberrant RNase L which caused an unnatural (unexpected) cleavage of ribosomal RNA in a typical polyacrylamide gel (PAGE) assay. Also, these eight patients had below normal levels of 2-5A synthetase before therapy. These patients responded most dramatically to dsRNA therapy in terms of improvement in IQ, MRI, etc., whereas the two patients without the biochemical defect had marginal responses.

TABLE 4

Coordinate Responses (Physiologic, Biochemical and Cognitive)
In Patients With Cerebral Dysfunction
With 2–5 A/RNase L Pathway Lesions A. Patients have decreased IQ. Following dsRNA (200–700 mg every 2 or 3 days given IV) IQ improves up to 50 points within 6 to 9 months.
B. MRI stabilizes or improves.
C. WAIS-R, WMS, MMPI improve, within 9–18 months in many cases.
D. NK (Natural Killer) cell, immunological status stabilizes or improves.
E. Virologic "burden" decreases as evidenced by decrease in the number of peripheral blood cells containing infectious particles of herpes-6 virus.
F. Increased performance associated with improved exercise tolerance (prolonged ability to remain on treadmill) and improved oxygen consumption.
G. Correction of 2–5 A/RNase L pathway defect often is a leading indicator that precedes clinical response by 4–12 weeks or longer.

Diagnosis is conveniently conducted from a sample of the patients blood to analyze the peripheral blood cells for enzymatically deficient 2-5'A using the procedures described by Carter et al in *The Lancet*, (ref. 1). The aberrance once noted is compared to the test results of otherwise healthy individuals, and is corrected by the exogenous administration of dsRNA, preferably a mismatched dsRNA, to improve the patient's clinical condition and restore cognitive abilities. During and at the conclusion of therapy, the patient is followed to ascertain his/her improvement on a cellular level, which usually precedes the clinical improvement by several weeks, and to determine the amount of dsRNA, if any, needed to maintain a normal 2-5'A synthetase/RNase L pathway and restore/maintain the patient's cognitive skills.

Diagnostic Procedures

The in vivo concentration of 2'-5'A molecules in normal individuals and subjects with chronic cerebral dysfunction is assessed as follows: Ethanol-soluble fractions of patient samples (Ficoll-Hypaque-purified peripheral blood lymphocytes) were analyzed for their 2-'5'A content in 2'-5'A core-cellulose assays (affinity chromatography) with poly U-$\{^{32}P\}$-pCp. In this assay, the ability of 2'-5'A-activated RNase L to hydrolyze poly(U) is used to determine the concentration of functional 2'-5'A.

Reference values were established by testing 15 normal subjects with no recent history of viral infections as evidenced by lack of fever, absence of constitutional symptoms, rashes, etc. Concentrations of their lymphocyte 2'-5'A levels were determined using calibration curves obtained with authentic 2'-5'A molecules.

The dsRNA may be a complex of a polyinosinate and a polycytidylate containing a proportion of uracil bases or guanidine bases, e.g., from 1 in 5 to 1 in 30 such bases (poly I.poly($C_{4-29}$x>U or G)).

The dsRNA may be of the general formula $rI_n.r(C_{11-14},U)_n$ or $rI_n.r(C_{12},U)_n$. Other suitable examples of dsRNA are discussed below.

By "mismatched dsRNA" are meant those in which hydrogen bonding (base stacking) between the counterpart strands is relatively intact, i.e., is interrupted on average less than one base pair in every 29 consecutive base pair residues. The term "mismatched dsRNA" should be understood accordingly.

The mismatched dsRNAs preferred for use in the present invention are based on copolynucleotides selected from poly ($C_n$,U) and poly ($C_n$,G) in which n is an integer having a value of from 4 to 29 and are mismatched analogs of complexes of polyriboinosinic and polyribocytidilic acids, formed by modifying $rI_n.rC_n$ to incorporate unpaired bases (uracil or guanidine) along the polyribocytidylate ($rC_n$) strand. Alternatively, the dsRNA may be derived from poly(I).poly(C) dsRNA by modifying the ribosyl backbone of polyriboinosinic acid ($rI_n$), e.g., by including 2'-O-methyl ribosyl residues. The mismatched complexes may be complexed with an RNA-stabilizing polymer such as lysine and cellulose. These mismatched analogs of $rI_n.rC_n$, preferred ones of which are of the general formula $rI_n.(C_{11-14},U)_n$ or $rI_n1.r(C_{29},G)_n$, are described by Carter and Ts'o in U.S. Pat. Nos. 4,130,641 and 4,024,222 the disclosures of which are hereby incorporated by reference. The dsRNAs described therein generally are suitable for use according to the present invention.

Other examples of mismatched dsRNA for use in the invention include:

poly (I).poly ($C_4$,U)
poly (I).poly ($C_7$,U)
poly (I).poly ($C_{13}$,U)
poly (I).poly ($C_{22}$,U)
poly (I).poly ($c_{20}$,G)
poly (I).poly ($c_{29}$,G) and
poly (I).poly $C_{p23}$ G>p Another class of dsRNAs suited to the practice of this invention are short dsRNAs of defined structure, for example oligonucleotides of the formula:

5'lock–$(I)_n$–lock 3'

3'lock–$(C)_m$–lock 5' where m and n are each more than 5 and less than 100, I is inosine monophosphate, C is cytidine monophosphate, and where the locks in one strand are complementary to locks in the opposite strand, or an oligonucleotide of the structure:

5'lock–$[(I)_xA]_j$–lock 3'

3'lock–[(C)_yU]_k–lock 3' where x and y are each more than 5 and less than 25, j and k each at least 1 and less than 10, I and C are as identified above, A is a nucleotide which is not I, and U is a nucleotide which base pairs with A.

Alternatively, the short oligonucleotide may have the structure:

5'(I)_n–hinge–(C)_m3' where n, m, I and C are as defined above.

These oligonucleotides may have substitutions in one strand not complementary to nucleotides in the opposite strand. Preferably these oligonucleotides are stabilized by internal registers of complementary heteropolymer and desirably the lock or hinge or both contain regions of complementary heteropolymer. These oligonucleotides desirably have single-stranded tails. These oligonucleotides are described in more detail in U.S. patent application Ser. No. 07/181,385 filed Apr. 14, 1988 to Gillespie and Crater and in corresponding PCT/US89/02172, the disclosures of which are hereby incorporated by reference.

In addition, 2'-5'A concentration and molecular size may be quantitated by high pressure liquid chromatography (HPLC). Also, ribosomal RNA cleavage assays may be used to assess biological functionality (activity) of the 2'-5'A-synthesized by the patient in vivo or to determine the level of activated RNase L in patient samples. Peripheral mononuclear blood cells are the preferred cells for analysis.

Patients having chronic cerebral dysfunction are treated with intravenous infusions of 200 to 700 mg of rI.r($C_{11-14}$,U) as required, e.g., once a week to as often as daily and 2'-5'A enzyme levels increase in association with clinical improvement. The amount of dsRNA administered and the frequency of administration will be guided by the 2'-5'A synthetase levels measured in conjunction with the patient's clinical improvement, particularly return of cognitive functions. Amounts of dsRNA administered will provide a level of from 0.01 to 1,000 micrograms of dsRNA per milliliter of the patient's systemic blood circulation immediately following administration measured at a point distal from the point of infusion.

References (1) Carter, W. A., Brodsky, I., Pelligrino, M. G. et al, Clinical, Immunological and Virological Effects of Ampligen, a Mismatched double-stranded RNA, in Patients with AIDS or AIDS-Related Complex, 1987, *The Lancet*, June 6: 1286–1292

(2) Kariko, K., Sobol, R. W., Suhadolnik, L. et al, Phosphorothioate Analogues of 2',4'-oligoadenylate. Enzymatically Synthesized 2'5'-oligoadenylate Dimer and Trimer: Unequivocal Structural Assignment and Activation of 2',5'-oligoadenylate Dependent Nuclease, 1987, *Biochemistry* 26: 7127–7135

(3) Wreschner, D. H., James T. C., Silverman, R. H. et al, Ribosomal RNa Cleavage, Nuclease Activation and 2-5 (ppp(A2'p)n A) in Interferon-Treated Cells, 1981, *Nuc. Ac. Res.*, 9: 1571–1581

(4) Salahuddin, S. Z., Ablashi, D. V., Markham, P. D. et al, Isolation of a New Virus, HBLV, in Patients with Lymphoproliferative Disorders, 1986, *Science*, 596–603

(5) Strauss, K. I, Strayer, D. R. and Gillespie, D., Detection of poly(I):poly($C_{12}$,U), Mismatched double-stranded RNA Intravenous Infusion, 1990, *J. Pharmacy and Pharmacol.*

(6) DuBois, E. E. et al, *Southern Med. Journal*, Vol. 77, pp. 1376 (1984)

(7) Imborlen, J. B. et al, *Archives Internal Medicine*, Vol. 103, pp. 406 (1959)

(9) Josephs, S. F. et al, *Science*, Vol. 234, pp. 601 (1986)

(9) Ablashi, D. V. et al, *Nature*, Vol. 329, pp. 207 (1987).

What is claimed is:

1. A method of diagnosing for the presence of neuro-cognitive disorders associated with systemic immunological malfunction in a human patient comprising assessing the level of intracellular RNase L in a sample of the patient's peripheral blood and comparing same to predetermined levels of RNase L in healthy individuals, aberrant RNase L levels as compared with those in healthy individuals indicating the presence of neuro-cognitive disorders associated with systemic immunological malfunction.

2. A method of distinguishing chronic cerebral dysfunction from primary psychological or neuropsychiatric disorders resembling same in a person comprising assessing the level of intracellular RNase L in a sample of the patient's peripheral blood and comparing same to predetermined levels of RNase L in healthy individuals, aberrant RNase L levels indicating the presence of chronic cerebral dysfunction.

* * * * *